US012673239B2

(12) United States Patent
Määttä et al.

(10) Patent No.: US 12,673,239 B2
(45) Date of Patent: Jul. 7, 2026

(54) SENSORS-BASED ADAPTATION OF TRAINING PROGRAM

(71) Applicant: Polar Electro Oy, Kempele (FI)

(72) Inventors: Harri Määttä, Kempele (FI); Tero Posio, Kempele (FI); Mika Rahja, Kempele (FI); Daniela Olstad, Kempele (FI); Katri Loukusa, Kempele (FI); Jonna Puurunen, Kempele (FI); Topi Korhonen, Kempele (FI)

(73) Assignee: Polar Electro Oy, Kempele (FI)

( * ) Notice: Subject to any disclaimer, the term of this patent is extended or adjusted under 35 U.S.C. 154(b) by 925 days.

(21) Appl. No.: 17/866,092

(22) Filed: Jul. 15, 2022

(65) Prior Publication Data

US 2023/0068647 A1 Mar. 2, 2023

(30) Foreign Application Priority Data

Aug. 20, 2021 (EP) ..................................... 21192278

(51) Int. Cl.
*A63B 24/00* (2006.01)
*G16H 20/30* (2018.01)

(52) U.S. Cl.
CPC ......... *A63B 24/0075* (2013.01); *G16H 20/30* (2018.01); *A63B 2024/0065* (2013.01);
(Continued)

(58) Field of Classification Search
CPC ........ A63B 24/0075; A63B 2024/0068; A63B 2024/0071; A63B 24/0062; A63B 24/00; A63B 2024/0065
See application file for complete search history.

(56) References Cited

U.S. PATENT DOCUMENTS 10,360,806 B2    7/2019  Jang et al.
2012/0277891 A1*  11/2012  Aragones ............. G09B 19/003
                                           700/91

(Continued)

OTHER PUBLICATIONS

Extended European Search Report received for EP Patent Application Serial No. 21192278.6 dated Feb. 10, 2022, 5 pages.

*Primary Examiner* — Jerry-Daryl Fletcher
(74) *Attorney, Agent, or Firm* — FisherBroyles, LLP

(57) ABSTRACT

A computer-implemented method for adapting a training program of a user, including: storing a database including measurement data of physical exercises the user has performed, the measurement data including at least one of heart activity measurement data and motion measurement data; receiving a user input to select a weekly template for the training program, the weekly template including a training schedule including a plurality of pre-programmed repeating exercises on the weekly template; receiving a user input indicating a repeating exercise the user indicates to perform outside the training program; acquiring, from the database on the basis of the user input indicating the repeating exercise, measurement data of past one or more physical exercises of the repeating exercise; determining, on the basis of the measurement data, a training effect of the past one or more physical exercises and determining at least one repeating physical exercise of the training schedule providing a training effect closest to the training effect of the past one or more physical exercises; adapting the training schedule by replacing the determined at least one repeating physical exercise of the training schedule with exercises of the repeating exercise the user indicates to perform outside the training program; and outputting, via a user interface, instructions for the user to follow the adapted training schedule.

19 Claims, 6 Drawing Sheets

(52) U.S. Cl.
CPC ................. *A63B 2024/0068* (2013.01); *A63B 2024/0071* (2013.01)

(56)                           References Cited

U.S. PATENT DOCUMENTS

2017/0368413  A1 *  12/2017   Shavit ................ A63B 24/0075
2020/0179757  A1      6/2020   Toivonen et al.

* cited by examiner

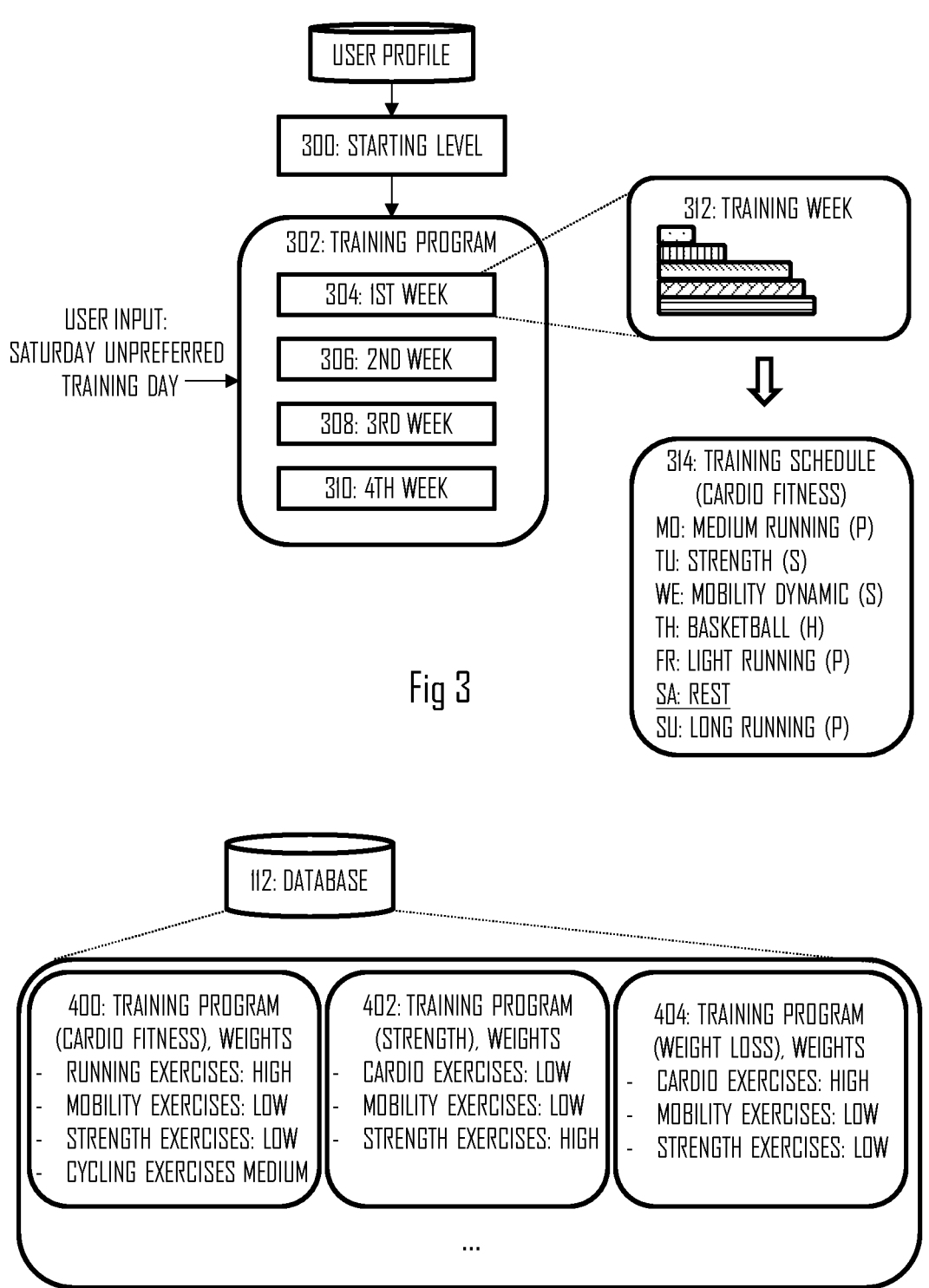

USER PROFILE

300: STARTING LEVEL

302: TRAINING PROGRAM

304: 1ST WEEK

306: 2ND WEEK

308: 3RD WEEK

310: 4TH WEEK

USER INPUT:
SATURDAY UNPREFERRED
TRAINING DAY

312: TRAINING WEEK

314: TRAINING SCHEDULE
(CARDIO FITNESS)
MO: MEDIUM RUNNING (P)
TU: STRENGTH (S)
WE: MOBILITY DYNAMIC (S)
TH: BASKETBALL (H)
FR: LIGHT RUNNING (P)
SA: REST
SU: LONG RUNNING (P)

Fig 3

112: DATABASE

400: TRAINING PROGRAM
(CARDIO FITNESS), WEIGHTS
- RUNNING EXERCISES: HIGH
- MOBILITY EXERCISES: LOW
- STRENGTH EXERCISES: LOW
- CYCLING EXERCISES MEDIUM

402: TRAINING PROGRAM
(STRENGTH), WEIGHTS
- CARDIO EXERCISES: LOW
- MOBILITY EXERCISES: LOW
- STRENGTH EXERCISES: HIGH

404: TRAINING PROGRAM
(WEIGHT LOSS), WEIGHTS
- CARDIO EXERCISES: HIGH
- MOBILITY EXERCISES: LOW
- STRENGTH EXERCISES: LOW

SENSORS-BASED ADAPTATION OF TRAINING PROGRAM

CROSS-REFERENCE TO RELATED APPLICATION

This application claims benefit and priority to European Application No. 21192278.6, filed Aug. 20, 2021, which is incorporated by reference herein in its entirety.

BACKGROUND

Technical Field

The invention relates generally to physiological activity measurements, such as heart rate or motion measurements. More particularly, the present invention relates to using such measurements to adapt a training program.

SUMMARY

A training program can be understood as a long-term plan to perform exercises to meet a program target. The program target may be gaining fitness, training for a particular training event such as a marathon or dropping weight. There exist solutions for adapting the training program on the basis of measurements performed on a user during exercises of the training program and/or between the exercises. For example, a training program may be adapted on the basis of the user's capability of meeting program targets during the training program. Another example is adaptation of an exercise planned for today on the basis of measured sleep quality. Poor sleep quality reduces capabilities of the user to benefit from a high-intensity exercise. However, further improvements to the use of the measurements to adapt the training program are needed. For example, known solutions do not flexibility to adapt the training program according to physical exercises performed by the user on a regular basis, e.g. sports hobbies. Such exercises are only taken into account when determining a fitness level of the user but it is forgotten that the user would often like to keep his/her hobbies.

The invention is defined by the independent claims. Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

Embodiments of the present invention are described below, by way of example only, with reference to the accompanying drawings, in which

FIG. 3 illustrates an embodiment of a training schedule of a training program;

FIG. 4 illustrates classification of physical exercises in various training programs;

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
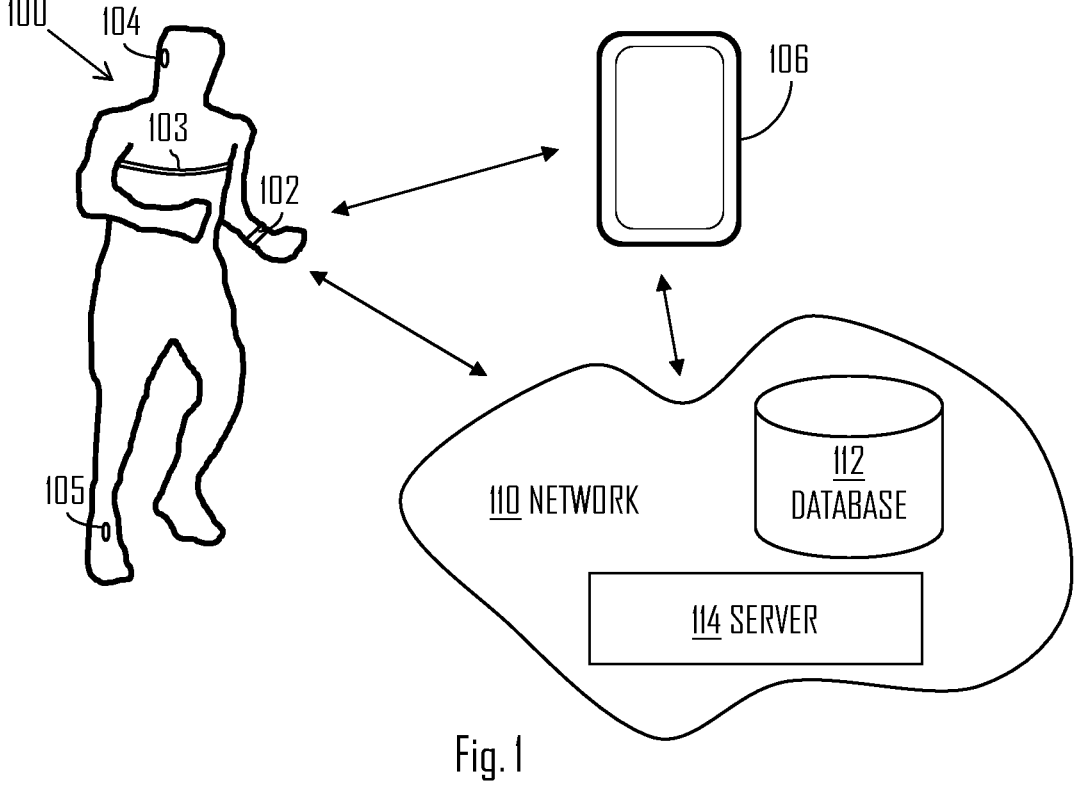
FIG. 1 illustrates a scenario to which embodiments of the present invention may be applied.

FIG. 1 illustrates a heart activity measurement system to which embodiments of the invention may be applied. Referring to FIG. 1, heart activity of a user 100 may be monitored by the user 100 using a portable or wearable electronic device, such as a wrist device 102. The wrist device 102 may comprise a heart activity measurement circuitry configured to determine user's 100 heart activity, such as a heart rate for example. The heart activity measurement circuitry may comprise an optical heart activity sensor, such as a PPG (photoplethysmography) sensor, configured to measure heart activity of the user 100. The optical heart activity sensor may detect the user's 100 heart activity by optical heart rate measurement, which may comprise sending a light beam towards body tissue of the user, and measuring the bounced and/or emitted light from the body tissue of the user 100. The body tissue of the user 100 may be, for example, skin of the user 100. The light beam may alter when travelling through the user's 100 veins and the alterations may be detected by the optical heart rate activity sensor. By using the detected data, the wrist device 102, may determine user's 100 heart activity, such as heart rate for example. Another known solution to measure the heart activity is an electrocardiogram (ECG) sensor configured to measure electric activity of the user's heart non-invasively. The ECG sensor may comprise electrodes configured to be coupled with the user's skin at any body part. A typical location for the ECG sensor is chest to which the ECG sensor 103 may be attached by means of a strap, or the ECG sensor 103 may be coupled to an apparel such as a shirt.

The heart activity measurement circuitry may comprise a bioimpedance sensor, wherein the bioimpedance sensor is configured to measure user's 100 heart activity. The bioimpedance measurement may be based on transmitting a radio signal into user's 100 skin, and observing changes in the radio signal due to impedance changes caused by, for example, blood volume changes. Thus, the user's 100 heart activity, such as heart rate, may be determined by the heart activity circuitry from the data produced by the bioimpedance sensor.

Further, besides these types of heart activity sensors, also other types of biosignal measurement sensors may be embedded into the heart activity measurement circuitry. These types include but are not limited to the following: a Laser Doppler-based blood flow sensor, a magnetic blood flow sensor, an Electromechanical Film (EMFi) pulse sensor, a polarization blood flow sensor.

The wrist device 102 may comprise a motion measurement circuitry configured to measure motion of the wrist device 102, wherein the motion measurement circuitry may comprise one or more motion sensor(s). The motion circuitry may be configured to measure the motion of the wrist device 102 in relation to the body tissue of the user 100. Thus, the motion circuitry may provide information about the connection of the wrist device 102 to the wrist of the user 100.

Further, the motion measurement circuitry may be configured to detect motion induced by the user 100 to the wrist device 102 by moving hand in which the user 100 wears the wrist device 102. The motion measurement circuitry may use other motion measurement data, such as location data of the user, to determine user's 100 motion. The location data may be acquired by means of a global navigation satellite system (GNSS) receiver or another positioning or motion analysis system. Examples of GNSSs are Global Positioning System (GPS) and Galileo. Some examples of the motion analysis system include a video-camera-based motion capture system, an ultra-wideband (UWB) technology based radar system, and an indoor positioning system based on some forms of radars or scanning.

In an embodiment, the motion sensor(s) comprise at least one of the following: an accelerometer, a magnetometer, and a gyroscope. The state-of-the-art knows several implementations of such motion sensors so more detailed description is omitted.

In an embodiment, the motion measurement circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion measurement circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the measurement system may further comprise the external sensor device(s) 103, 104, 105 used by the user 100. The external sensor device(s) 103 to 105 may comprise sensors, such as a heart rate transmitter configured to be positioned at the chest (sensor 103) or at an ear (sensor 104), a stride sensor 105, a positioning sensor, a cadence sensor and a power sensor, to mention a few. The heart rate transmitter 103 may comprise at least one electrical, optical and/or bioimpedance sensor to measure user's 100 heart activity.

The external sensor device(s) 103 to 105 may generate measurement data during physical exercises performed by the user. The physical exercise may be launched in the wrist device, and the wrist device may control the sensor devices described above to conduct the measurements during the exercise and to transmit the measurement data to the wrist device 102, to a portable electronic device 106 and/or to a server 114 storing the user's user account. The server computer 114 may reside beyond one or more networks 110, including telecommunication and/or computer networks. The portable electronic device 106 may be a mobile phone, a smart phone, a palm device, a tablet computer, phablet or a portable digital assistant, for example. In some cases, the wrist device 102 may operate as a hub that collects the measurement data during the exercise and then synchronizes the measurement data with the portable electronic device 106 and/or the server 114. The wrist device 102, the portable electronic device 106 and/or the server 114 may comprise at least one processor configured to process the measurement data including the heart activity measurement data and/or the motion measurement data into a set of metrics describing the user's 100 performance during the exercise. The metrics as such may be metrics known in the art. For the purpose of the embodiments described herein, metrics such as heart rate variability, heart stroke volume, speed, power, cadence, and a training load may be employed. The heart rate variability is a known parameter that describes beat-to-beat variability of heart beats and a state of the user's nervous system. The training load or training effect of the exercise may be based on measured intensity and duration of the exercise. The intensity of a session is measured using heart rate and/or motion, and the calculation is further affected by personal characteristics, such as age, sex, weight, maximum oxygen intake (VO2max), and training history. Additionally, personal aerobic and anaerobic threshold values may be used in the calculation. A sport type of the exercise is taken into account via a sport-specific factor, which improves the calculation accuracy. The training effect can be further modified to match with a particular purpose, as described in some embodiments below.

The external sensor device(s) 103 to 105, the wrist device 102, the portable electronic device 106 and/or the server 114 may each further comprise a communication circuitry, such as wireless communication circuitry, configured to enable sensor data transfer between the external sensor device(s) 104, wrist device 102, portable electronic device 106 and/or the server 114. The communication circuitry may employ suitable communication protocols such as Bluetooth® technology.

In an embodiment, the external sensor device(s) 104 comprise at least one external sensor device.

Further, the wrist device 102 and/or the portable electronic device 106 may comprise a memory, wherein the memory may be used by the devices to store the measurement data. The server 114 may use a database 112, such as a training database, to store the said measurement data. The database 112 may reside in the network 110. At least some of the contents of the database may be synchronized between the devices 102, 106, 114 so that relevant measurement data is available to carry out the embodiments described below.

In an embodiment, at least some functions of the external sensor device(s) 103 to 105 are comprised in the wrist device 102. For example, the ECG sensor or the positioning sensor may reside in the wrist device, as well as at least one motion sensor.

As described in Background, known solutions for designing a training program for the user do not consider a situation that the user would have other regular activities besides the training program. For example, the user may have a sports hobby such as badminton, basketball, yoga, etc. and, additionally, the user would like to train for an event or to generally improve some aspect of his/her fitness. A conventional solution is to build the training program, and the user would have to manually balance between the exercises of the regular activities and exercises of the training program. For example, it is a conventional situation where the training program suggests a certain exercise for a particular day when the user has his/her regular activities. In such a case, the suggested exercise is simply left unconducted and, in cases where there is high difference in a training load of the suggested exercise and the exercise of the user's hobby, the conducted exercise may degrade the performance towards one or more targets of the training program. The mismatches between the suggested training program and the user's exercises conducted outside the training program may cause further adverse effects on the user's fitness and health.

Figure 2:
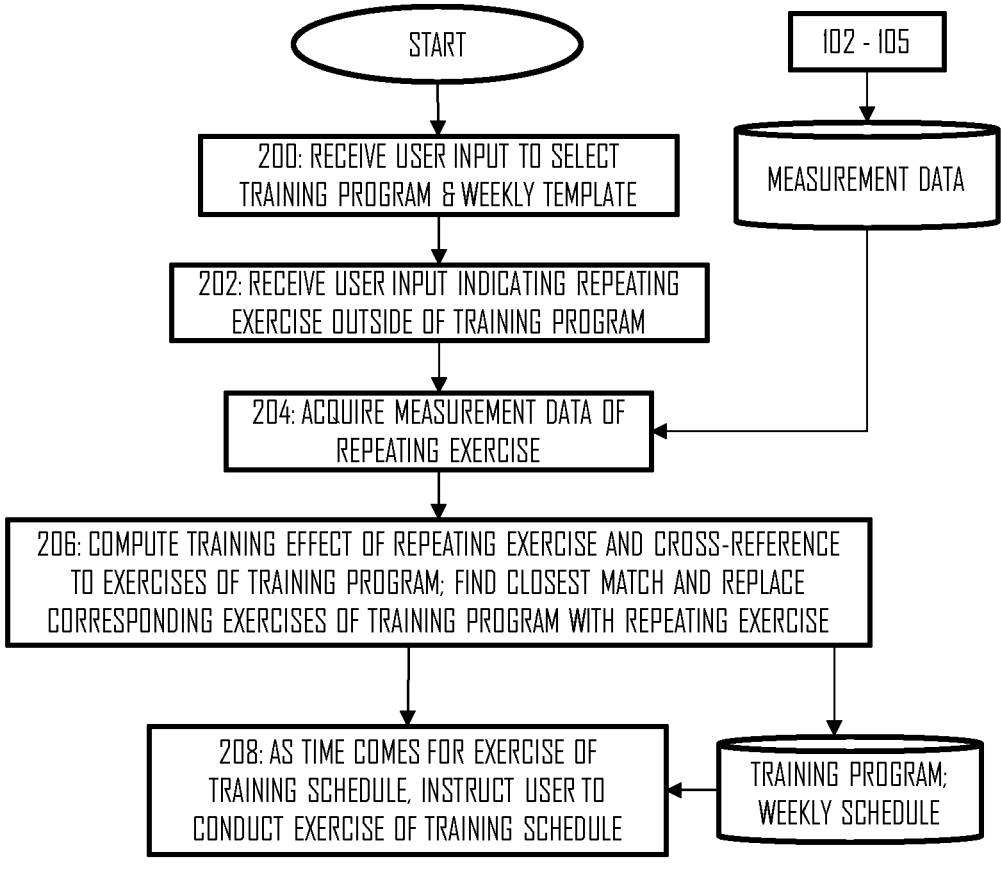
FIG. 2 illustrates an embodiment of a computer-implemented method for managing a training program.

FIG. 2 illustrates a flow diagram of a computer-implemented method for adapting a training program of a user. The method may be carried out in any one of the devices 102, 106, 114 having a suitable user interface with the user. Referring to FIG. 2, the method comprises: storing a database comprising measurement data of physical exercises the user has performed, the measurement data comprising at least one of heart activity measurement data and motion measurement data; receiving (block 200) a user input to select a weekly template for the training program, the weekly template comprising a training schedule comprising a plurality of pre-programmed repeating exercises on the weekly template; receiving (block 202) a user input indicating a repeating exercise the user indicates to perform outside the training program; acquiring (block 204), from the database on the basis of the user input indicating the repeating exercise, measurement data of past one or more physical exercises of the repeating exercise; determining (block 206), on the basis of the measurement data, a training effect of the past one or more physical exercises and determining at least one repeating physical exercise of the training schedule providing a training effect closest to the training effect of the past one or more physical exercises; adapting (block 206) the training schedule by replacing the determined at least one repeating physical exercise of the training schedule with exercises of the repeating exercise the user indicates to perform outside the training program; and outputting (block 208), via a user interface, instructions for the user to follow the adapted training schedule.

A technical effect is that the user's regular exercises the user intends to perform outside the training program, such as sports hobbies, are integrated into the training program and they replace the exercises of the training program that have the most similar training effect for the training program, e.g. for a purpose of the training program or for a target of the training program. Accordingly, improved overall training guidance and training effect for the training program can be achieved. Further, adverse effects on the user's health and fitness described above can be avoided.

As indicated above, the repeating exercise indicated in block 202 is not in the training original training schedule of the weekly template.

In an embodiment, the training program is a continuing training program with no end date. This distinguishes from other training programs that guide the user, via the exercises of the training program, towards an end date where there is a sports event such as a competition. A theme or purpose of the training program may be, for example: lose weight, improve strength, or improve cardio fitness. Each theme may have one or more specific training targets and specific physical exercises designed to guide the user towards the one or more training targets. For example, the weight loss program may include light or medium cardio workouts such as walking or running with low heart rate, and exclude or have few high-intensity workouts such as strength exercises. The cardio fitness program may include a high number of running or cycling exercises in the weekly training schedule and with various training intensities and, further, some supporting exercises between the cardio exercises. The supporting exercises may include mobility exercises and strength exercises. The training program aiming for the strength improvement may comprise circuit or strength exercises and some supporting exercises such as mobility exercises, and some or few cardio exercises such as walking exercises or low-intensity running or cycling exercises.

With respect to the mobility exercises, they may include exercise that improve the user's flexibility and ability to employ greater range of motion of joints and muscles. The mobility exercises may include dynamic mobility exercises where the user is instructed to improve the mobility via repetitive motion that stretch the muscles and joints in a dynamic manner. Such exercises may include inch worm, Ferris wheel, scorpion, and hip roll exercises, among many others. Static mobility exercises aim for the same purpose but with static stretching where the stretching position is maintained for a certain time interval.

In the context of this description, a cardio exercise refers to a cardiovascular exercise such as walking, running, cycling, rowing, jogging, or elliptical training. Such a cardio exercise may be aerobic, anaerobic, or a combination of aerobic and anaerobic intervals during the exercise. In some contexts, such cardio exercises are defined as endurance or aerobic exercises but it should be understood that cardio exercises may include high-intensity exercises or intervals that improve anaerobic fitness and even maximum speed. A general purpose of such exercises is to increase heart rate and to maintain the heart rate at the increased level for a long time, thus distinguishing from strength exercises where the heart rate may rise but typically only for a very short time.

The training program may be planned for a determined time period into the future, e.g. the weekly training schedule may be planned and displayed to the user four weeks from the present date, and the weekly training schedule may be updated weekly (e.g. after Sunday) on the basis of the user' performance past week. An example of the training program is illustrated in FIG. 3. The database 112 may store the user's user profile including the above-described personal characteristics such as age, weight, and the measurement data of past exercises. Upon receiving the user input to generate the training program 302, the user profile may be used (particularly the measurement data) to determine a starting level 300 of the training program 302. The measurement data and/or other parameters of the user profile may be used to determine the user's fitness level in the selected theme of the training program 302. For example, if the theme is weight loss, a lower starting level may be generally assigned to a person having a higher weight. Accordingly, the training schedule may include lighter exercises on the lower starting level and longer or harder exercises on the higher starting levels. As described above, the training program may comprise four weekly training schedules 304 to 310 and generated on the basis of the determined starting level and the regular exercises the user has indicated to perform on top of the training program. The training schedule may have a distribution of the exercises that each have a plan in terms of exercise intensity, e.g. in terms of a heart rate distributed into heart rate zones, stroke volume distributed into stroke volume zones, or in running or cycling (cardio) exercises speed distributed into speed zones. The exercises may be classified according to another rule, for example on the basis of a theme of the exercises (cardio exercise, strength exercise, mobility exercise, . . . ). The theme of the training program may then define a target distribution amongst the different classes in the weekly training schedule. This is illustrated as a target distribution of exercises in a training week plan 312 in FIG. 3. Bars with various filling represent the different classes and the width of the bar illustrates a target amount of exercising in each class. For example, if the classes are defined in terms of heart rate zones, the particular training week plan 312 may be understood to target a greater amount of low-intensity training (the lowest bar) and only some amount of high-intensity training (the highest, dotted bar). This is a typical distribution for a cardio fitness program where aerobic or endurance training is emphasized. The training schedule 314 illustrated in FIG. 4 then comprises the exercises of the weekly training schedule. As illustrated in the training schedule 314, an exercise planned for Thursday has been replaced by an exercise of the user's hobby which is basketball in this case, indicated as a hobby by 'H' in FIG. 3. As described above, the basketball exercise may replace an exercise of the training schedule that provides the most similar training effect for the purpose of cardio fitness. The exercise replaced by the basketball exercise may be an interval running exercise, for example. Table below illustrates some examples of exercises of the training program that can be replaced by various hobby exercises that are outside the training program.

| Hobby Exercise | Replaced Exercise of Training Program |
| --- | --- |
| Basketball, badminton, floorball | Interval running exercise |
| Yoga | Mobility static exercise (stretching) or mobility dynamic exercise |
| Cycling | Long, running exercise, dynamic mobility exercise, recovery exercise (low intensity) |
| Cross-country skiing | Aerobic running exercise |
| Weightlifting, gym | Strength or circuit exercise |
| Spinning | Interval exercise or medium-intensity running exercise |

As described above, the similarity between the training effects of the replacing and replaced exercise may be determined on the basis of the measurement data. A training benefit may be used as one way of classifying the similarity in the training effects. The training benefit can be found in products by Polar Electro®, and it is based on the accumulation of time at different heart rate zones, i.e. energy consumption at the various heart rate zones. The following training benefit categories may be provided:

| Training Benefit Class | Definition |
| --- | --- |
| Maximum training | Improved sprint speed and the nervous system of muscles, and efficiency. Typically a long session with much time spent on high-intensity zones |
| Tempo training | Improved aerobic fitness, speed, and ability to sustain high intensity effort for longer. Typically medium or long session with quite a lot of time spent on high-intensity zones |
| Steady state training | Improved the endurance of muscles and aerobic fitness. Typically a lot of time spent on aerobic zones (medium intensity below an anaerobic threshold) |
| Basic training, long | Long, low-intensity session improves basic endurance and body's ability to burn fat during exercise. |
| Recovery training | Supporting exercise. Short, light this allows body to adapt to training. Short time on low-intensity zone(s). |

Further categories of the training benefit can be provided. As an alternative to the training benefit, another metric may be used, for example a cardio load or a muscle load. The cardio load is based on training impulse calculation (TRIMP), a commonly accepted and scientifically proven method to quantify training load. A cardio load value tells how much strain a physical exercise or a training session has put on a cardiovascular system. The higher the cardio load, the more strenuous the training session was for the cardiovascular system. The cardio load may be calculated after every physical exercise from the heart rate measurement data and duration of the physical exercise, and it is commonly used in many commercially available products. The muscle load tells how much muscles were strained during a physical exercise. The muscle load helps to quantify the training load in high-intensity training sessions, such as short intervals, sprints and hill sessions, and strength and circuit exercises when the heart rate reacts too slowly to the changes in the training intensity. The muscle load shows the amount of mechanical energy (kJ) produced during the physical exercise. The muscle load reflects an energy output, not the energy input it took to produce particular effort. In general, the fitter the user is, the better the efficiency between the energy input and energy output. The muscle load is calculated based on measured power and duration of the exercise. In case of running, also the weight is taken into calculation. Since the muscle load is calculated from power measurement data, a running or cycling power sensor may be used to calculate the muscle load.

The exercises of the training schedule may also be classified accordingly by using any one of the metrics described in the previous paragraph. This is enabled by the plan for each exercise in the training schedule, wherein the plan defines intensity zones and an intensity profile for the exercise, e.g. in terms of the heart rate, stroke volume, power, or speed. Since the plan readily defines the accumulation of heart rate, speed, stroke volume, or another intensity metric and various intensity zones, the training benefit of the plan can be estimated directly from the intensity distribution to the various intensity zones. A light (low exertion) training benefit may be estimated for a planned exercise where the training is directed mainly to the low-intensity zone(s). A highly exerting training benefit may be estimated for a planned exercise that includes at least a certain amount of exercising on the high-intensity zone(s). The same applies to the equivalents of the training benefit in this context, i.e. the cardio load or the muscle load. Accordingly, block 206 may comprise determining the training benefit, cardio load, or muscle load of the user's repeating exercise that is outside the training program, which can be determined from the measurement data of one of the repeating exercises or as an average of the measurement data of multiple repeating exercises in the database 112. This training benefit, cardio load, or muscle load may then be cross-referenced with training benefits, cardio loads, or muscle loads in the training schedule of the training program, and an exercise having the same training benefit, cardio load, or muscle load may be selected to be replaced by the repeating exercise providing the same training benefit, cardio load, or muscle load. The 'phase' of the training program may also be shifted so that it matches with the date of the repeating exercise. For example, if the user is practicing on Thursdays basketball that would replace the interval running exercise and the training schedule would initially place the interval exercise on Saturday, block 206 may include shifting the training schedule by two days such that the interval running exercise would also be scheduled to Thursday and thus be replaced by the basketball exercise. The other exercises of the training program would be shifted in the same manner so that the order of exercises remains intact, thus following the training program.

Let us then describe further the adaptation of the training schedule on a weekly basis. The user's ability to keep up with the training plan may thus be evaluated weekly and the processing system executing the embodiments of FIG. 2 may provide the user with feedback and adapt the training schedule for the following weeks on the basis of the performance of the past week or weeks. Evaluation of the user's performance in the past week is done, for example, in the following way. If the user is training according to a training program which aim to develop his aerobic condition, the focus in evaluation may be in the cardio exercises of the training schedule and the user's performance in them. However, all exercises of the training schedule and the user's performance therein and, optionally, any additional exercise the user has conducted and from which measurement data is available may be evaluated Both the intensity (computed from the heart rate and/or motion measurement data) and duration of training at each intensity zone (training intensity distribution) may be monitored, at a weekly level. Metrics computed from measurement data from all exercises from one week may be aggregated and evaluated to determine the user's weekly performance with respect to the plan and targets illustrated in the view 312 of FIG. 3. If the volume at different intensities of the training falls far behind the training plan, e.g. more than a determined threshold amount, the user is encouraged to exercise more and/or in a different manner. If the intensity (and volume) is close or equal to the training plan, the user may be provided positive feedback and/or virtual rewards. If the intensity (and volume) of the training plan is significantly exceeded, the user is reminded of the importance of recovery and slow progression in training volumes. At low intensities, it is acceptable to exceed the planned training volume, even by a significant amount, but at the high-intensity level it is more critical to follow the planned amount of training. If the user consistently exceeds the target amount at the high-intensity levels, the user has a risk for injury or overreaching.

As described above, the training program may have a training target or training targets defining a purpose of the training program in terms of an effect on the user. In case of the weight loss being the purpose, the training target(s) may include: a target defining a determined amount of training at one or more low-intensity zones (e.g. heart rate zones or speed zones), a target defining a determined amount of low-intensity exercises to be conducted by the user, and/or a target defining a maximum amount of training at high-intensity zones and/or a maximum number of high-intensity exercises to be conducted. In a case where the purpose of the training program is to improve cardiovascular fitness, the training target(s) may include: a target set defining a determined amount of training at least a determined amount at each intensity zone including both low-intensity zone(s) and high-intensity zone(s), a target defining a determined amount of performing at least a determined amount of cardio exercises to be conducted by the user, and/or a target defining that the user should perform at least one mobility exercise or a strength exercise during the week.

Physical exercises of the training schedule may be classified into priority exercises and supportive exercises on the basis of training effects of the physical exercises of the training schedule on the training target or targets. The training schedule 314 of FIG. 3 illustrates an example of the classification for the training program having the purpose of 'improving cardio fitness'. Running exercises may then be categorized as the priority exercises (indicated by 'P' in FIG. 3) while the other exercises (strength, mobility, . . . ) may be categorized as supportive exercises (indicated by 'S' in FIG.

3). In general, a priority exercise may be defined as an exercise that, when conducted, has a high effect on reaching the training target(s). If the purpose is strength training, conducting strength exercises or circuit exercises have a great effect on reaching that purpose. Similarly, if the purpose is improving cardio fitness, cardio exercises are then classified as the priority exercises. A supportive exercise may be defined as an exercise that supports the priority exercises in reaching the training targets. The supportive exercises may be understood such that they improve the user's physiological properties such that the user is capable of performing better in the priority exercises. For example, a strength or mobility exercise has a relatively low direct effect on improving the cardiovascular fitness but they improve the user's muscular system, joints, flexibility and such so that the user is able to get a higher benefit from the cardio exercises. Such classification into priority and supportive exercises may be used for various purposes, as described in embodiments below.

In an embodiment illustrated in FIG. 3, when generating the training program or during the training program, the user may provide a user input indicating preferred training days or training weeks and unpreferred training days or training weeks on the weekly template. The above-described classification may then be used by allocating the priority exercises on the preferred training days or training weeks and the supportive exercises on the unpreferred training days or training weeks or on days or weeks with no preference. The days or weeks with no preference may be preferred over the unpreferred training days or weeks when allocating the supportive exercises. In other words, resting days of the training program may be primarily allocated to the unpreferred training days. Accordingly, the training program may be adapted to the user's weekly schedule and routines, e.g. to allow the user to have a relaxed training schedule for a day or a week when the user is not able to conduct the exercises.

The user may be allowed to edit the training schedule within determined boundaries. For example, the user may be allowed to change the order of the exercises within the weekly schedule. Certain rules may be applied, such as high-intensity exercises are not allowed on the same or subsequent days to allow appropriate recovery. The user may be allowed to add or remove exercises. The boundaries may be defined such that a minimum number of priority exercises remain in the training schedule.

In an embodiment, the training schedule is adapted to a measured and predicted alertness of the user. There exist various solutions for measuring the user's alertness and physiological capability to conduct the exercise and to predict the future alertness on the basis of the measurements. Sleep analysis is one such parameter. Sleep data may be gathered from a period longer than just one night, and it enables estimation of the user's alertness for the next day. Heart rate variability and analysis of sleep stages during the sleep are ways to measure sleep quality that directly maps to the capability to conduct exercises. It is not only possible to determine the user's current alertness level, but also to predict his future alertness level, or estimate user's typical rhythm in alertness. This information could be utilized in adapting the training schedule to match with user's alertness and schedule high-intensity exercises to days of where the observed history shows the user to have high alertness. The training schedule may further propose an hour when to carry out the exercise. The hour may also be determined on the basis of the measured alertness. For example, if the measurements indicate that the user is most alert during morning hours, the exercises are proposed to be started during the morning hours.

As described above, the training schedule comprises, before and after said replacing, a plurality of exercises of different exercise types serving for the purpose of the training program. And as described above, one or more training targets may be defined per training program, and the one or more training targets may be comprised in a set of pre-specified different training targets. The training targets may be defined in terms of the intensity levels in the view 312 of FIG. 3. Alternatively, or additionally, the priority/supportive classification of the exercises may be used by defining in the training targets a target number of priority exercises and a target number of priority exercises to be conducted. For example, at least a determined number of priority exercises need to be conducted during the week to meet the training target. Other forms of training targets are equally possible.

In an embodiment of FIG. 2, the method provides, per exercise type, a weight of the training effect of the exercise type for each training target in the set of different training targets. The weight may be defined in terms of the priority and supportive exercise but another, non-binary weighting may be employed. The training effect may be the above-described training effect or the training benefit, for example. The weight may be different for at least two different training targets in the set of different training targets, and at least two different exercise types may have different weights of the training effect per training target. FIG. 4 illustrates the weighting according to an embodiment. The weights may be stored in the database 112. The weights may be numeric within a determined range, e.g. between zero and one, or they may be binary having two values (low and high or equivalently supportive and priority) or tertiary having three values (low, medium, and high), the absolute values being designed as desired. FIG. 4 illustrates the weights per training program, using the themes described above. As illustrated, the training program 400 for improving the cardio fitness may assign high weights to corresponding priority exercises such as running exercises, and assign low weights to supportive exercises such as the strength and mobility exercises. Some cardio exercises may be given a lower weight, e.g. the medium weight. The training program 402 for improving the strength may assign high weights to corresponding priority exercises such as the strength or circuit exercises, and assign low weights to supportive exercises such as the cardio exercises. The training program 404 for losing weight may assign high weights to corresponding priority exercises such as low-intensity running exercises, and assign low weights to supportive exercises such as the strength exercises. The corresponding classification may be built for other training programs in a straightforward manner by the person skilled in the art.

The personal repeating exercise of the user may also be categorized as the priority or the supporting exercise, and a corresponding weight (low or high) may be given to it. For example, if the user has the cardio training program 400 and basketball or similar high-intensity training replacing a (priority) cardio exercise in the training schedule, a high weight may be given to it. Similarly, if the user has the strength-improving training program and gym as the repeating exercise, it may replace the (priority) strength exercise and thus be given a high weight while yoga may be given a low weight. In an embodiment, the personal repeating exercise is (always) given the same weight as the exercise it replaces in the training schedule.

By using the weights and the measurement data, a training effect per conducted exercise may be computed and the user's progress towards said training target can be determined on the basis of the computed training effect per conducted exercise. Let us describe a few examples. As described above, one training target may be defined in terms of a number of conducted priority exercises and, optionally, a number of supportive exercises. At the end of the week, the method may compute the number of conducted priority exercises and compare the number with a target number of priority exercises. The supportive exercises may count as less than one priority exercise in this scenario, thus having a low weight. For example, two conducted supportive exercises may count as one conducted priority exercise. If the number of conducted priority exercises meets the target number, the user has achieved the training target. Otherwise, the user has not achieved the training target. Another training target may be defined in terms of the training intensity zones, and the amount of time accumulated in each intensity zone during the conducted exercises may be computed. Time-accumulation of a priority exercise may have a higher weight than time-accumulation of a supportive exercise, e.g. a time unit spent on a particular intensity zone during a supportive exercise may be a fraction (less than one) of a time unit spent on the particular intensity zone during a priority exercise. If the total time-accumulation in each zone meets the respective target times per zone, the user is deemed to have met the training target. If there is one or more intensity zones where sufficient accumulation has not been reached during the week, it may be determined that the user has not reached the training target.

If the user is deemed to have reached the training target(s), the method may evaluate the current fitness of the user and redesign the training schedule for the next three weeks and design the following fourth week ahead. For example, if the user is deemed to have reached the fitness of ascending to the next higher training level, the future exercises may be designed to provide a greater demand on the user so as to provide constant improvement. On the other hand, if the user is deemed to not have reached the training target(s), the method may also evaluate the current fitness of the user and redesign the training schedule for the future three weeks and design the fourth week ahead. For example, if the user is deemed to have performed so much below the target and the fitness is deemed to have degraded so that the training level should be degraded, the future exercises may be designed to provide a lower demand on the user so as to provide a reasonable and reachable solution for improvement towards the purpose of the training program.

Figure 5:
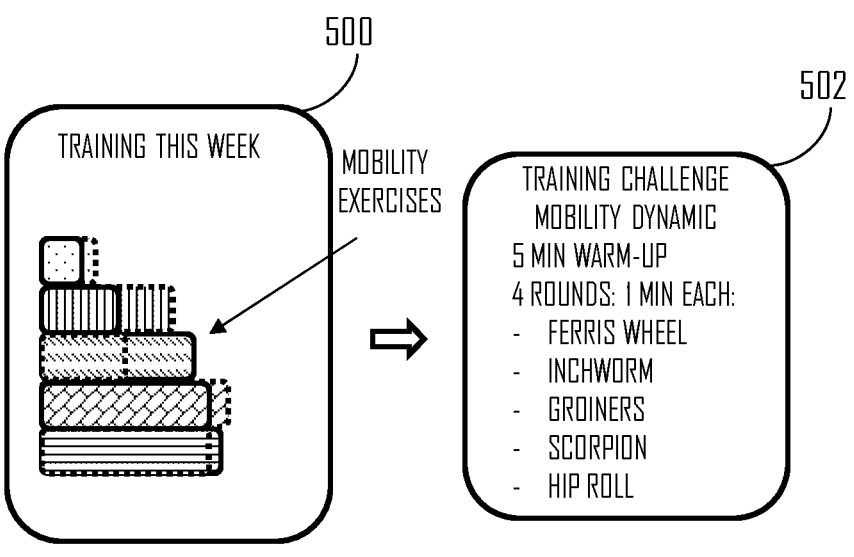
FIGS. 5 and 6 illustrate embodiments for guiding a user to meet training targets of a training program.

In an embodiment, the method of FIG. 2 further comprises determining, on the basis of the measurement data, accumulation of conducted exercises per exercise type comprised in the training schedule and, upon detecting that the user has not conducted at least one exercise type, generating a challenge exercise of the at least one exercise type and outputting a proposal of the challenge exercise to the user via the user interface, wherein the challenge exercise is outside of the training schedule. The exercise types have been listed above and they may be, for example: running exercise or a sub-type thereof, strength exercise, circuit exercise, or mobility exercise (dynamic or static/stretching). Sub-types of the running (or cycling) exercises include interval, medium-intensity, long low-intensity, short low-intensity, and high-intensity maximum speed running/cycling exercise, for example. Yet as another example, the priority/supportive classification may be used as the exercise type. FIG. 5 illustrates this embodiment. In the embodiment of FIG. 5, a training accumulation view 500 may illustrate the accumulation of exercises in classes of the exercise type. A solid bar represents the training target accumulation for the particular exercise type, and the dashed bar represents the measured accumulation, as computed from the measurement data. As illustrated, the user has reached the target in other exercise type classes but the mobility. Upon detecting that the user has not reached the training target in a particular exercise type, the method may generate an additional exercise in the particular exercise type and output, via the user interface, a message to the user to propose the additional exercise with a determined plan for the exercise. The plan may be designed in the method so that conducting the challenge exercise would remedy the deficiency between gained accumulation and the target accumulation in the particular exercise type. For example, if the particular exercise type is the mobility, as illustrated, the method may generate an additional mobility exercise with a plan that would enable increasing the accumulation in the particular category to the target amount. This may be conducted by selecting a duration and contents of the exercise accordingly, e.g. a number of rounds of exercises as illustrated in the view 502 (four rounds in this case). The display views 500, 502 may be provided in a display of the wrist device 102 or the portable device 106, and the user may be guided during the tasks of the challenge exercise, as known in the art. A technical effect of this embodiment is further improved training guidance to meet the training targets of the training program. This distinguishes from solutions where the user generally instructed to "train more". The proposal of the additional exercise may not cause any changes to the present or future training schedule as such. For example, proposing an additional mobility exercise may replace or render obsolete no mobility exercise of the future training schedule. Instead of generating the additional exercise, the method may output an instruction highlighting the next exercise of the particular exercise type in the future training schedule. In such manner, the training schedule need not to be modified in any manner which simplifies the guidance towards the priority exercise(s) important for the desired target(s) of the training program.

Instead of the exercise types, another classification may be used in the embodiment of FIG. 5. For example, the bars in the display view may represent the different intensity zones described above. Upon detecting that a certain intensity zone is below its training target, the method may generate the challenge exercise with contents that increase the accumulation on one or more intensity zones that are below the target, without significantly adding accumulation on the intensity zones where the user has already reached the target. As described above, overreaching is not necessarily beneficial.

Figure 6:
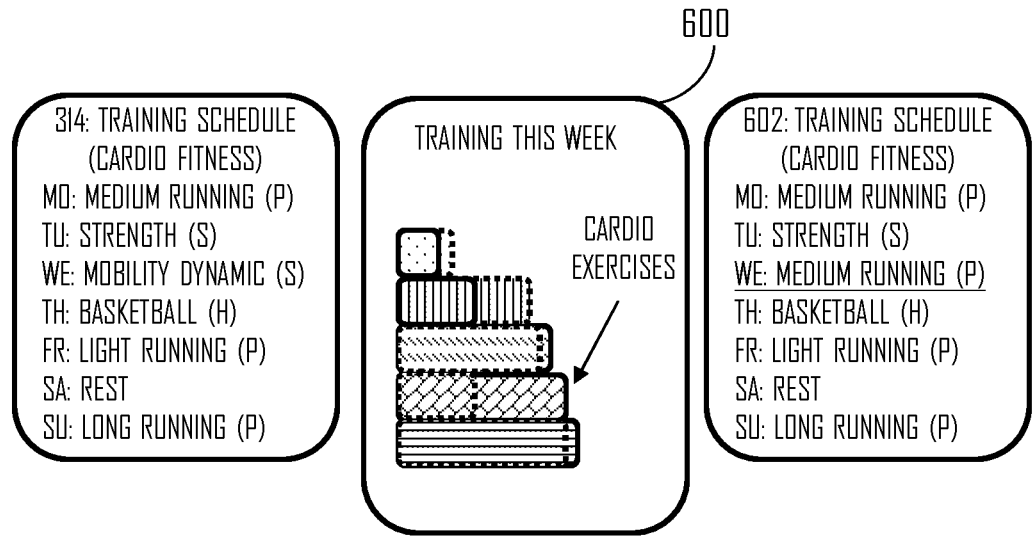

Further related to the classification of the exercises to the priority and supportive exercises, the classification may be used in guiding the user towards the training target(s). In an embodiment, the method comprises determining, on the basis of the measurement data, accumulation of conducted exercises comprised in the training schedule and, upon detecting that the user did not conduct at least one priority exercise of the training schedule, replacing at least one supportive exercise by the at least one priority exercise in the future training schedule. This may be carried out in connection with the weekly evaluation of the performance and adapting the training schedule for the next week and, optionally, weeks after that. FIG. 6 illustrates this embodiment. FIG. 6 illustrates two training schedules 314 and 602 for consecutive weeks. Initially, the training schedules 314, 602 may be identical for the consecutive weeks. However, after the expiry of the week of the training schedule 314, the method may comprise the evaluation of the user's performance during the week, e.g. according to the embodiments described in connection with FIG. 5. Upon detecting that the user has not reached the target for a determined priority exercise type, e.g. cardio exercises as illustrated in the display view 600 that is a priority exercise in the cardio fitness program (see training schedule 314), the method may adapt the training schedule 602 of the next week by replacing at least one supportive exercise with a priority exercise of the training program. In this case, the mobility exercise is replaced by a running exercise on Wednesday. Similar modification may be performed for the next week as well. In this manner, the method may adapt the future training schedule to contain more priority exercises than on the previous week.

With respect to the feedback to the user after the weekly evaluation, the accumulation in particular exercise types and/or exercise intensities described above may be translated into a score. The scoring may be dependent on the classification of the exercise types (priority and supportive) and the target intensities. For example, training the priority exercise types and/or the training intensities that have a higher target value may gain more points than training the supportive exercises and/or the training intensities having a lower target value. Further relating to the adaptation of the training schedule, the training schedule may be adapted on the basis of a user input indicating a need to adapt the training schedule. Such an input may be the user indicating that he/she is sick or injured. In such a case, the training program may cancel the exercises at least for a determined number of days. The user may indicate the number of days via the user interface. Other inputs causing the adaptation may be performing a test by using the sensor system described above, e.g. a fitness test or an orthostatic test. If the test indicates a substantial change in the performance with respect to a previous test, the adaptation of the training schedule may be required towards the direction of the change, degradation meaning adaptation towards an easier training schedule. Further inputs may include an overall training load estimate indicating the user's training load over the conducted exercises, or the sleep analysis. If the training load indicates that the user has trained more than he/she is physiologically capable and about to overreach, the training schedule may be relaxed, e.g. by replacing one or more high-intensity exercises with exercises having a lower intensity. The training load and the recovery analysis may use the respective features and functions present in the state-of-the-art sports training computers such as Polar Vantage V. For example, the following principles may be followed. For those days when training load status indicates "Overreaching" (injury and illness risk active), productive cardio sessions (and/or strength workouts) are not recommended. The user may still choose to perform such an exercise, change it to a lighter exercise, or just skip it. Program adaptation may happen based on recovery information in following situations with priority order (from highest to lowest): For those days when the recovery level is "Not recovered", productive cardio sessions are not recommended. User may still choose to perform it, change it to lighter or just skip it. For those days when muscle recovery level is "Not recovered", strength sessions are not recommended. User may still choose to perform it, change it to lighter or just skip it. For those days when the sleep analysis is "Poor" or "Very poor", productive cardio sessions are not recommended. User may still choose to perform it, change it to lighter or just skip it.

With respect to the adaptation based on health status, program adaptation may happen based on the health status information input by the user in following situations with priority order (from highest to lowest): If the user is sick, the user is advised to rest. If the user is recovering from sickness, the user is advised to train lighter. Productive (high intensity) cardio targets are replaced with light cardio target. Strength targets are replaced with mobility target. If user is slightly sick, user is advised to train lighter. If user is injured, user is advised to train if injury allows. If user is slightly injured, user is advised to train if injury allows.

Above, some concrete training targets are defined. From another aspect, the training targets may be more abstract but directly linked to the purpose of the respective training programs. Accordingly, the set of training targets may comprise at least one of the following training targets: improve aerobic fitness, improve strength, lose weight, improve mobility, and train for a specified event or competition. The training target may thus equal to the purpose of the training program. The priority exercises and supportive exercises may then be classified as follows:

improve aerobic fitness: priority exercises comprise at least one aerobic running exercise and supportive exercises comprises at least one strength exercise;

improve strength: priority exercises comprise at least one strength exercise and supportive exercises comprise at least one aerobic exercise;

lose weight: priority exercises comprise a plurality of aerobic exercises and supportive exercises comprise at least one strength exercise;

improve mobility: priority exercises comprise a plurality of different types of mobility exercises and supportive exercises comprise at least one aerobic exercise;

train for an event or a competition: priority exercises comprise a plurality of exercise of the same sports type as the event or the competition, and supportive exercises comprise at least one exercise of an exercise type different form the sports type of the event or the competition. For example, if the event is a running competition, the priority exercises comprise running exercises that are of the same sports type. However, a cycling exercises may be counted as a supportive exercise although it has a similar training effect from the perspective of improving cardio or aerobic fitness. Accordingly, the cycling and running exercises may be priority exercises when the training target is to improve the aerobic fitness but have different priorities with another training target. The same applies to the other exercise types. The classification between priority and supportive exercise is determined on the basis of the training target and the training benefit of the exercise towards that target.

As described above, the training program may be an endless training program having no specific end date. Naturally, the user may choose to end the program at any time by operating the user interface of the portable device 106 or by connecting to the server 114 via a computer.

Figure 7:
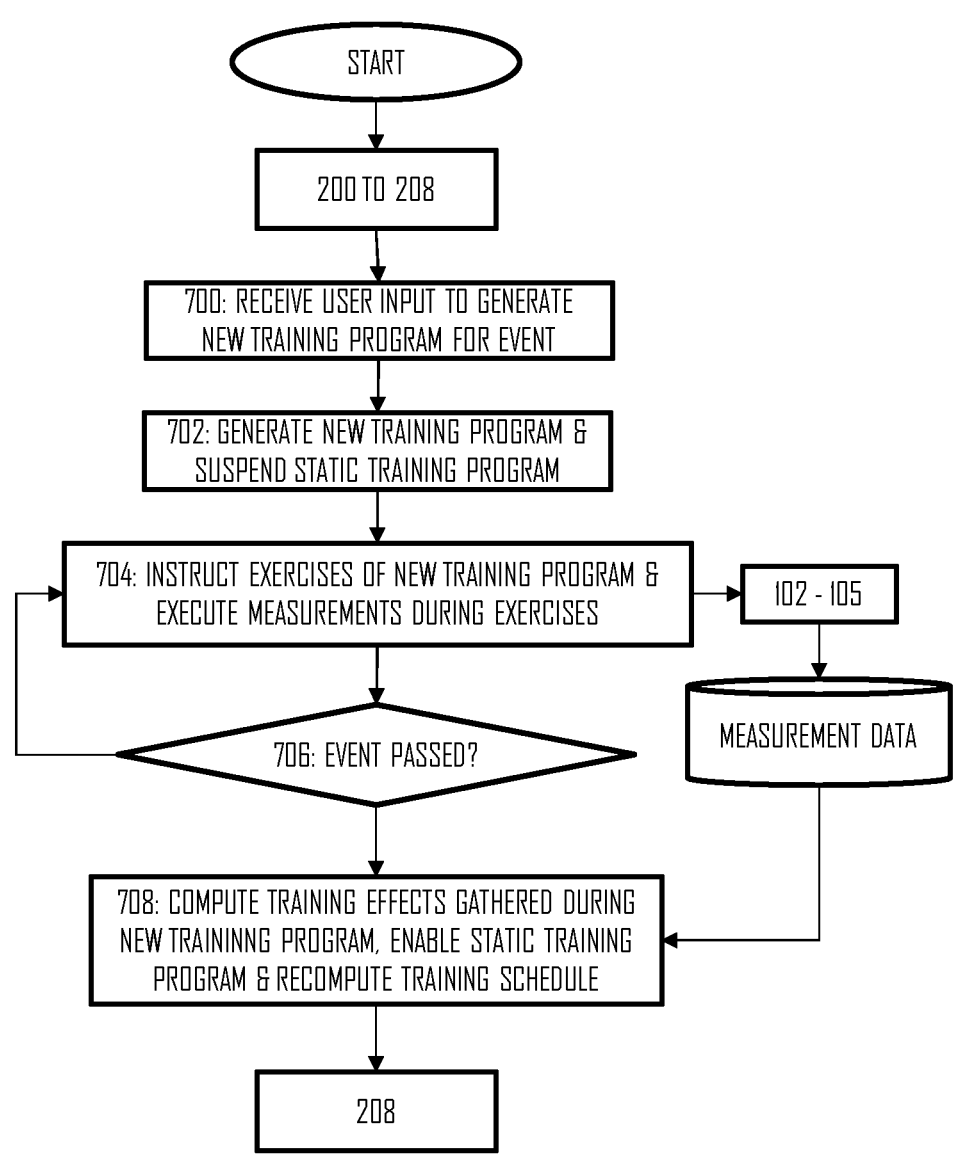
FIG. 7 illustrates an embodiment for managing multiple training programs.

There may arise a need for the user to start another training program having a different purpose that has a predetermined time span, e.g. a training program aiming to train the user for an event or a competition, e.g. a running or cycling race. FIG. 7 illustrates an embodiment of the method of FIG. 2 to manage the endless training program described above in connection with such an event. Blocks 200 to 208 may be carried out according to any one of the above-described embodiments. In block 700, a user input for generating a new training program for training for an event having a specified date is received. Upon receiving the input, the method generates (block 702), on the basis of the measurement data gathered before and/or during the training program, the new training program having the specified end date. Further, upon generating the new training program, the endless training program is suspended for the duration of the new training program. During the new training program, the user is instructed by the wrist device and the portable device 106 to conduct physical exercises of the new training program (block 704), and the wrist device controls the sensors to measure and generate measurement data during the physical exercises of the new training program. The new training program may follow principles of state-of-the-art training program models, e.g. a training program for running a marathon on the specific date. Upon the specified date has passed ('yes' in block 706), the endless training program that was suspended is again enabled. Furthermore, new training schedules may be computed (block 708) for the endless training program on the basis of the measurement data acquired during the new training program. The computation may follow the above-described principles. For example, a training effect for said endless training program may be computed by using the measurement data acquired during the physical exercises of the new training program. Accordingly, the beneficial or adverse effects of the new training program on the user's fitness for the endless training program are taken into account when the user reactivates the endless training program. For example, if the endless training program has been to improve strength and the new training program is training for a marathon, the user may have dropped a substantial amount of strength exercises for the duration of the marathon training. Therefore, continuing blindly from the state where the endless training program was suspended would be a risk for injuries, because the strength may need to be rebuilt. On the other hand, if the endless training program is improving aerobic fitness, the marathon exercise would work for the benefit of that purpose, and the user's fitness at the end of the new training program for that purpose would probably be higher at the end of the new training program than what it was at the beginning. Therefore, continuing blindly from the state where the endless training program was suspended would probably result in degradation of the user's fitness. Accordingly, the benefit of the new training program is taken into account directly into the endless training program when it is once again enabled after the end date of the new training program.

The user may choose to change the purpose of the training program at any time. For example, the user may choose to change the theme of his/her training from improving aerobic fitness into improving strength. In such a case, the current training program may be ended, and the new training program with the new training target(s) and training schedules may be generated according to the principles described above. Since the purpose of the training is different, so is the classification of the physical exercises into the supportive and priority exercises in the respective embodiments. Accordingly, the user's fitness for the new purpose may be recomputed with the respective changes. Since the logic in the classification between the priority and supportive exercises changes, it is possible that the user's fitness level for the new training program is lower than the user's fitness for the old training program, unless the user has already deviated from the proposed training schedule. Regardless of that, the measurement data is available for the evaluation of the user's fitness for the new training program, and the training target(s) may be set appropriately on the basis of the measurement data such that the training target(s) is/are on the appropriate level.

Figure 8:
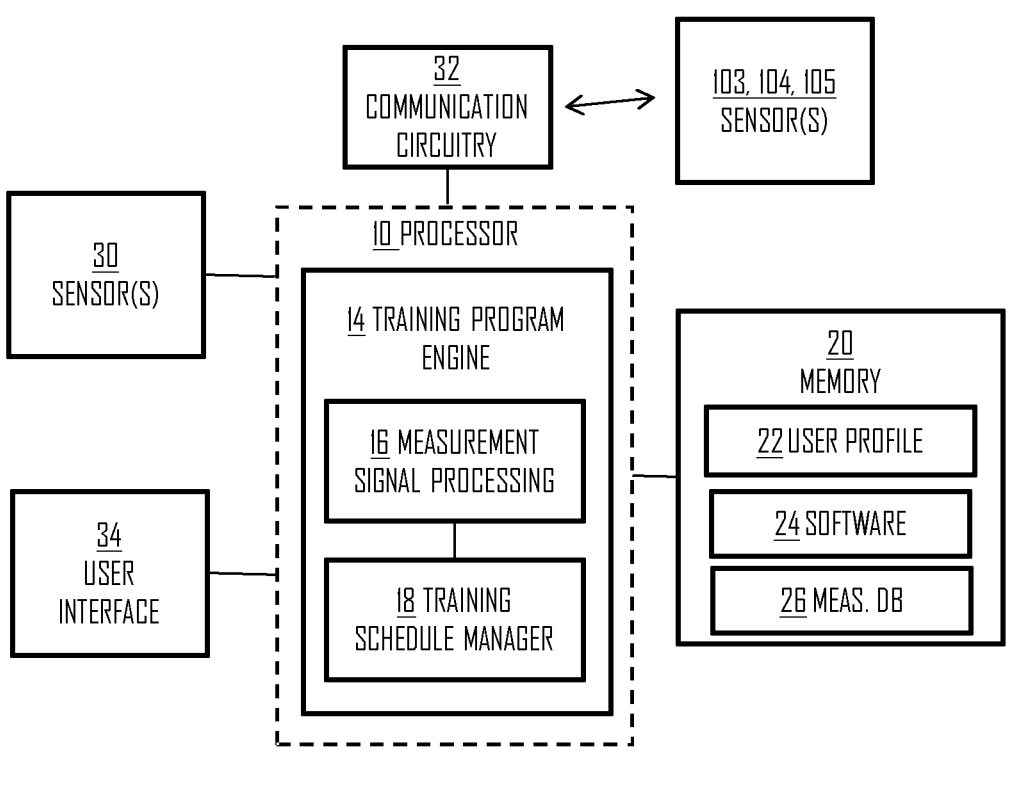
FIG. 8 illustrates a block diagram of an apparatus according to an embodiment of the invention.

FIG. 8 illustrates a block diagram of an apparatus according to an embodiment of the invention, comprising a processing system configured to perform the method of claim 2 or any one of the embodiments thereof described above. Referring to FIG. 8, the apparatus may be the wrist device 102, the portable electronic device 106 or the server 114. The processing system may comprise at least one processor 10 and at least one memory 20. The apparatus may further comprise a user interface 34 comprising a display screen or another display unit, an input device such as one or more buttons and/or a touch-sensitive surface, and an audio output device such as a loudspeaker. In some embodiments, the user interface 34 comprises a haptic output device configured to provide haptic indications to the user 100. In the case of the apparatus being the server computer, the user interface may be provided via a client device such as the computer or the portable device 106 communicating with the server computer.

The processor 10 may comprise a training program engine 14 configured to manage the training programs by controlling the procedure of FIG. 2 or any one of the embodiments thereof. The training program engine 14 may comprise a measurement signal processing circuitry 16 configured to acquire the measurement data for the purposes of generating and/or adapting the training schedules. In embodiments where the apparatus is the wrist device, the circuitry 16 may control the external sensor devices 103, 104, 105 and/or internal sensor devices 30 to carry out the measurements and collect the measurement data from the sensor devices. As described above, the internal sensor devices 30 may comprise at least one heart activity sensor and/or at least one motion sensor provided in the wrist device. The training program engine 14 may further comprise a training schedule manager 18 configured to generate and adapt the training schedules according to the principles described above and on the basis of the measurement data acquired by the circuitry 16.

The apparatus may comprise a communication circuitry 32 connected to the processor 10. When the apparatus is the wrist device, the communication circuitry may comprise hardware and software suitable for supporting Bluetooth® communication protocol such as Bluetooth Smart specifications. It should be appreciated that other communication protocols are equivalent solutions as long as they are suitable for establishing a personal area network (PAN) with the sensors 103 to 105 or suitable for measurement scenarios described in this document. When, the apparatus is the wrist device or the portable device 106, the communication circuitry may comprise a radio modem and appropriate radio circuitries for establishing a communication connection with the other devices, e.g. server computer, the wrist device, or the portable device 106, depending on the implementation of the apparatus. Suitable radio protocols may include IEEE 802.11-based protocols or cellular communication protocols. In case the apparatus is the server computer, the communication circuitry 32 may comprise one or more computer network circuits operating, for example, according to Ethernet protocol. The processor 10 may use the communication circuitry 32 to transmit and receive frames or data according to the supported wireless communication protocol. The frames may carry a payload data comprising the above-described motion measurement data measured by one or more external motion sensors 103 to 105 or data between the devices 102, 106, 114. As described above, contents of the database 112 may be transferred for the purpose of managing the training program.

The memory 20 may store a computer program product 24 defining the computer program instructions for carrying out the method of FIG. 2 or any one of the embodiments thereof. The memory may further store a user profile 22 of the user 100 storing personal characteristics of the user 100, e.g. age, weight, the fitness level, etc. The memory may further store a measurement database 26 comprising the measurement data computed during and/or after the exercises of the training program, the repeating exercises of the user's hobby integrated into the training program and, in some embodiments, the measurement data acquired during other training programs of the user.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIGS. 2 to 7 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor, the memory, and the computer program code form processing means or comprises one or more computer program code portions for carrying out one or more operations according to any one of the embodiments of FIGS. 2 to 7 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 2 to 7 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A computer-implemented method for adapting a training program of a user, comprising:

storing a database comprising sensor-acquired measurement data of physical exercises the user has performed, the measurement data comprising at least one of heart activity measurement data and motion measurement data, wherein the measurement data has been acquired by a wrist device worn by the user during the physical exercises, the wrist device comprising at least one of a heart activity sensor and a motion sensor;

receiving a user input to select a weekly template for the training program, the weekly template comprising a training schedule comprising a plurality of pre-programmed repeating exercises on the weekly template;

receiving a user input indicating a repeating exercise the user indicates to perform outside the training program;

acquiring, from the database on the basis of the user input indicating the repeating exercise, measurement data of past one or more physical exercises of the repeating exercise;

computing, by a processor of the wrist device, on the basis of the measurement data, at least one quantitative training-effect parameter comprising at least one of a training benefit based on accumulated time in heart-rate zones, a cardio load computed from training impulse, and a muscle load computed from measured mechanical power and duration, and determining at least one repeating physical exercise of the training schedule providing a training effect closest to the training effect of the past one or more physical exercises;

automatically adapting, by execution of computer instructions, the training schedule by replacing the determined at least one repeating physical exercise of the training schedule with exercises of the repeating exercise the user indicates to perform outside the training program; and outputting, via a user interface, on a display of the wrist device, real-time instructions for the user to follow the adapted training schedule.

2. The method of claim 1, wherein the training program comprises a training target defining a purpose of the training program in terms of an effect on the user, the method further comprising:

classifying physical exercises of the training schedule into priority exercises and supportive exercises on the basis of training effects of the physical exercises of the training schedule on the training target; and using the classification in at least one of the following actions: building or modifying the training schedule; evaluating the user's performance on the basis of measurement data acquired during physical exercises of the training schedule.

3. The method of claim 2, further comprising:

receiving a user input indicating preferred training days or training weeks and unpreferred training days or training weeks on the weekly template; and allocating the priority exercises on the preferred training days or training weeks and the supportive exercises on the unpreferred training days or training weeks or on days or weeks with no preference.

4. The method of claim 2, wherein the training program comprises at least one training target of a set of pre-specified different training targets, the method further comprising:

providing, per exercise, a weight of a training effect of the exercise type for the at least one training target, wherein the weight is different for the priority exercise than for the supportive exercise; and computing, on the basis of the measurement data, a training effect per conducted exercise and determining user's progress towards said training target on the basis of the computed training effect per conducted exercise, the training effect weighted selected on the basis of whether the conducted exercise is the priority exercise or a supportive exercise.

5. The method of claim 2, further comprising determining, on the basis of the measurement data indicating conducted exercises of the training schedule, accumulation of conducted priority exercises and accumulation of supportive exercises comprised in the training schedule and, upon detecting that the user has not conducted at least one priority exercise, generating a challenge priority exercise and outputting a proposal of the challenge priority exercise to the user via the user interface, wherein the challenge priority exercise was not originally in the training schedule.

6. The method of claim 2, further comprising determining, on the basis of the measurement data, accumulation of conducted exercises comprised in the training schedule and, upon detecting that the user did not conduct at least one priority exercise of the training schedule, replacing at least one supportive exercise by the at least one priority exercise in the future training schedule.

7. The method of claim 2, wherein the at least one training target defines a purpose of the training program, and wherein the at least one training target is selected from a set of training targets comprising at least one of the following training targets: improve aerobic fitness, improve strength, lose weight, improve mobility, and train for an event or a competition, and wherein the priority exercises and supportive exercises are classified in at least one of a plurality of classes comprising:

improve aerobic fitness: priority exercises comprise at least one aerobic running exercise and supportive exercises comprises at least one strength exercise;

improve strength: priority exercises comprise at least one strength exercise and supportive exercises comprise at least one aerobic exercise;

lose weight: priority exercises comprise a plurality of aerobic exercises and supportive exercises comprise at least one strength exercise;

improve mobility: priority exercises comprise a plurality of different types of mobility exercises and supportive exercises comprise at least one aerobic exercise; and train for an event or a competition: priority exercises comprise a plurality of exercise of the same sports type as the event or the competition, and supportive exercises comprise at least one exercise of an exercise type different form the sports type of the event or the competition.

8. The method of claim 1, wherein the training program is a continuing training program with no end date.

9. The method of claim 8, further comprising:

receiving a user input generating a new training program for training for an event having a specified date and generating, on the basis of the user input and the measurement data, the new training program having the specified end date;

acquiring measurement data during physical exercises of the new training program; and suspending said training program for the duration of the new training program, upon the specified date has passed, enabling said training program and computing a training effect for said training program by using the measurement data acquired during the physical exercises of the new training program.

10. A computer system comprising:

at least one memory storing a database comprising sensor-acquired measurement data of physical exercises the user has performed, the measurement data comprising at least one of heart activity measurement data and motion measurement data, wherein the measurement data has been acquired by a wrist device worn by the user during the physical exercises, the wrist device comprising at least one of a heart activity sensor and a motion sensor; and a processing system configured to perform operations comprising:

receiving a user input to select a weekly template for the training program, the weekly template comprising a training schedule comprising a plurality of pre-programmed repeating exercises on the weekly template;

receiving a user input indicating a repeating exercise the user indicates to perform outside the training program;

acquiring from the database on the basis of the user input indicating the repeating exercise, measurement data of past one or more physical exercises of the repeating exercise;

computing, on the basis of the measurement data, at least one quantitative training-effect parameter comprising at least one of a training benefit based on accumulated time in heart-rate zones, a cardio load computed from training impulse, and a muscle load computed from measured mechanical power and duration, and determine at least one repeating physical exercise of the training schedule providing a training effect closest to the training effect of the past one or more physical exercises;

automatically adapting, by execution of computer instructions, the training schedule by replacing the determined at least one repeating physical exercise of the training schedule with exercises of the repeating exercise the user indicates to perform outside the training program; and outputting, via a user interface, on a display of the wrist device, real-time instructions for the user to follow the adapted training schedule.

11. The computer system of claim 10, wherein the training program comprises a training target defining a purpose of the training program in terms of an effect on the user, and wherein the processing system is further configured to perform operations comprising:

classifying physical exercises of the training schedule into priority exercises and supportive exercises on the basis of training effects of the physical exercises of the training schedule on the training target; and using the classification in at least one of the following actions: building or modifying the training schedule; evaluating the user's performance on the basis of measurement data acquired during physical exercises of the training schedule.

12. The computer system of claim 11, wherein the processing system is further configured to perform operations comprising:

receiving a user input indicating preferred training days or training weeks and unpreferred training days or training weeks on the weekly template; and allocating the priority exercises on the preferred training days or training weeks and the supportive exercises on the unpreferred training days or training weeks or on days or weeks with no preference.

13. The computer system of claim 11, wherein the training program comprises at least one training target of a set of pre-specified different training targets, and wherein the processing system is further configured to perform operations comprising:

providing, per exercise, a weight of a training effect of the exercise type for the at least one training target, wherein the weight is different for the priority exercise than for the supportive exercise; and computing, on the basis of the measurement data, a training effect per conducted exercise and determining user's progress towards said training target on the basis of the computed training effect per conducted exercise, the training effect weighted selected on the basis of whether the conducted exercise is the priority exercise or a supportive exercise.

14. The computer system of claim 11, wherein the processing system is further configured to perform operations comprising determining, on the basis of the measurement data indicating conducted exercises of the training schedule, accumulation of conducted priority exercises and accumulation of supportive exercises comprised in the training schedule and, upon detecting that the user has not conducted at least one priority exercise, generate a challenge priority exercise and outputting a proposal of the challenge priority exercise to the user via the user interface, wherein the challenge priority exercise was not originally in the training schedule.

15. The computer system of claim 11, wherein the processing system is further configured to perform operations comprising determining, on the basis of the measurement data, accumulation of conducted exercises comprised in the training schedule and, upon detecting that the user did not conduct at least one priority exercise of the training schedule, replacing at least one supportive exercise by the at least one priority exercise in the future training schedule.

16. The computer system of claim 11, wherein the at least one training target defines a purpose of the training program, and wherein the at least one training target is selected from a set of training targets comprising at least one of the following training targets: improve aerobic fitness, improve strength, lose weight, improve mobility, and train for an event or a competition, and wherein the priority exercises and supportive exercises are classified in at least one of a plurality of classes comprising:

improve aerobic fitness: priority exercises comprise at least one aerobic running exercise and supportive exercises comprises at least one strength exercise;

improve strength: priority exercises comprise at least one strength exercise and supportive exercises comprise at least one aerobic exercise;

lose weight: priority exercises comprise a plurality of aerobic exercises and supportive exercises comprise at least one strength exercise;

improve mobility: priority exercises comprise a plurality of different types of mobility exercises and supportive exercises comprise at least one aerobic exercise; and train for an event or a competition: priority exercises comprise a plurality of exercise of the same sports type as the event or the competition, and supportive exercises comprise at least one exercise of an exercise type different form the sports type of the event or the competition.

17. The computer system of claim 10, wherein the training program is a continuing training program with no end date.

18. The computer system of claim 17, wherein the processing system is configured to perform operations comprising:

receiving a user input generating a new training program for training for an event having a specified date and generating, on the basis of the user input and the measurement data, the new training program having the specified end date;

acquiring measurement data during physical exercises of the new training program; and suspending said training program for the duration of the new training program, upon the specified date has passed, enabling said training program and computing a training effect for said training program by using the measurement data acquired during the physical exercises of the new training program.

19. A computer program product embodied on a non-transitory distribution medium readable by a computer and comprising program instructions which, when loaded and executed by the computer, execute a computer process comprising:

storing a database comprising sensor-acquired measurement data of physical exercises the user has performed, the measurement data comprising at least one of heart activity measurement data and motion measurement data, wherein the measurement data has been acquired by a wrist device worn by the user during the physical exercises, the wrist device comprising at least one of a heart activity sensor and a motion sensor;

receiving a user input to select a weekly template for the training program, the weekly template comprising a training schedule comprising a plurality of pre-programmed repeating exercises on the weekly template;

receiving a user input indicating a repeating exercise the user indicates to perform outside the training program;

acquiring, from the database on the basis of the user input indicating the repeating exercise, measurement data of past one or more physical exercises of the repeating exercise;

computing, on the basis of the measurement data, at least one quantitative training-effect parameter comprising at least one of a training benefit based on accumulated time in heart-rate zones, a cardio load computed from training impulse, and a muscle load computed from measured mechanical power and duration, and determining at least one repeating physical exercise of the training schedule providing a training effect closest to the training effect of the past one or more physical exercises;

automatically adapting, by execution of computer instructions, the training schedule by replacing the determined at least one repeating physical exercise of the training schedule with exercises of the repeating exercise the user indicates to perform outside the training program; and outputting, via a user interface, on a display of the wrist device, real-time, instructions for the user to follow the adapted training schedule.

\* \* \* \* \*